United States Patent [19]
Kross

[11] Patent Number: 5,252,343
[45] Date of Patent: Oct. 12, 1993

[54] METHOD AND COMPOSITION FOR PREVENTION AND TREATMENT OF BACTERIAL INFECTIONS

[75] Inventor: Robert D. Kross, Bellmore, N.Y.

[73] Assignee: Alcide Corporation, Norwalk, Conn.

[21] Appl. No.: 854,286

[22] Filed: Mar. 20, 1992

[51] Int. Cl.$^5$ .................. A01N 59/00; A01N 59/08
[52] U.S. Cl. ................... 424/661; 424/662; 424/663; 424/664; 424/665
[58] Field of Search ............ 424/661, 665, 662, 663, 424/664

[56] References Cited

U.S. PATENT DOCUMENTS

| | | | |
|---|---|---|---|
| 2,071,091 | 2/1937 | Taylor | 167/17 |
| 3,123,521 | 3/1964 | Wentworth et al. | 167/17 |
| 3,386,915 | 6/1968 | Rutschi et al. | 210/62 |
| 3,826,826 | 7/1974 | Cantor et al. | 424/149 |
| 4,021,585 | 5/1977 | Svoboda et al. | 426/332 |
| 4,025,628 | 5/1977 | Dewey et al. | 424/249 |
| 4,507,285 | 3/1985 | Kuhne | 424/130 |
| 4,725,437 | 2/1988 | Kuhne | 424/130 |
| 4,737,307 | 4/1988 | Brown et al. | 252/106 |
| 4,829,129 | 5/1989 | Kelley | 525/326.9 |
| 4,956,184 | 9/1990 | Kross | 424/661 |
| 4,983,634 | 1/1991 | Corby | 514/622 |

OTHER PUBLICATIONS

Oliver, S. P. et al. "Prevention of Bovine Mastitis . . .", Journal of Dairy Science, 72 (11), pp. 3091-3097, (1989).
Drechsler, P. A., "Evaluation of a Chlorous Acid--Chlorine Dioxide Teat Dip . . ." Journal of Dairy Science, 73(8), Aug. 1990, pp. 2121-2128.
Chemical Abstracts 102 (13): 109684b, (1984).
Encyclopedia of Chemical Technology, 3rd ed., vol. 5 John Wiley & Sons, N.Y., 1979, pp. 612 and 628.
Masschelein, W. J. Chlorine Dioxide: Chemistry and Environmental Impact of Oxychlorine Compounds, 1979; Ann Arbor Science Publishers Inc., Michigan, pp. 5-6, 158-161 and 172-173.

Primary Examiner—Richard L. Raymond
Assistant Examiner—John D. Pak
Attorney, Agent, or Firm—Seed and Berry

[57] ABSTRACT

There is disclosed methods and compositions for preventing and treating bacterial infections, including mastitis, in the udder of a mammal. The compositions include chlorine dioxide in an amount ranging from 5 ppm to 1000 ppm, and have a chlorine dioxide to chlorite ratio of at least 5:1. Methods of the present invention include the infusion of the composition into the mammal's udder, and the formation of the compositions immediately prior to infusion.

17 Claims, No Drawings

METHOD AND COMPOSITION FOR PREVENTION AND TREATMENT OF BACTERIAL INFECTIONS

TECHNICAL FIELD

This invention relates generally to the prevention or treatment of bacterial infections in a mammal's udder, and more particularly to the prevention or treatment of bovine mastitis, including both "subclinical mastitis" and "clinical mastitis."

BACKGROUND OF THE INVENTION

Bacterial infections, particularly bovine mastitis, are the most costly, complex and difficult challenge to the dairy industry. In the United States alone, mastitis costs dairy farmers close to $3 billion a year, or about $300 per cow.

Mastitis is defined as an inflammation of the mammary gland, and occurs primarily as a result of infection by bacteria which gain entry to the udder via the teat canal. Mastitis is recognized to exist in two forms, "subclinical," where the infection is not directly evident by visual or physical inspection of either the milk or the mammary gland, and "clinical," which is diagnosed by the presence of visually detectable alterations in the milk (clots, discoloration) and glands (swollen, firm, warm, painful). Elevated levels of white cells in the milk, in response to the infection, are characteristic of mastitis. The common demarcation of 500,000 white cells per milliliter of milk separates "subclinical" and "clinical" mastitis.

It has been estimated that about 20 cases of subclinical mastitis occur for every case that, untreated, generally develops into overt clinical mastitis. Both subclinical and clinical forms affect milk production. Depending on the severity of the subclinical form, the production of milk by an infected cow can be as much as 20% less than that of a non-infected cow, and cases of subclinical disease can last for several months. On the other hand, the milk from a clinically-mastitic cow must be discarded, and in some cases the cow has to be destroyed (if the disease resists treatment). The cow may even die, often within 24 hours, following infection with certain coliform organisms.

Prior attempts to treat the mastitis infection have involved the infusion of an antibiotic into the udder (in the case of the clinical disease). Since treatment is commonly instituted prior to identification of the specific causative organism, it is important to select an antimicrobial which offers the greatest range of efficacy against the array of pathogens causing mastitis. Although certain organisms, such as *Streptococcus agalactiae* and *Staphylococcus aureus*, are the principle pathogens associated with infectious mastitis, a great number of environmental and contagious microorganisms are also known to cause this disease (e.g., coliforms, *Klebsiella pneumoniae, Actinomyces pyogenes, Corynebacterium bovis, Listeria monocytogenes, Pseudomonas aeruginosa,* other Staph. and Strep. species, and *Mycoplasma bovis*).

Despite a recognized need, no single antibiotic is presently available to the dairy industry that has demonstrated activity against all the mastitis associated organisms. Furthermore, all current antibiotic therapies for mastitis, which involve infusion into the infected quarter of the udder, result in a mandatory time period thereafter in which the cow's milk cannot be sold. This occurs because these antibiotics can remain in the cow's udder for many days after infusion, and contaminate the milk produced during that time. This contamination will significantly inhibit the growth of microorganisms in milk, particularly those used for processing the milk into cheese or yogurt. The antibiotics can also inhibit the intestinal flora of young children who consume large quantities of such milk. Residual antibiotics can also provoke allergic responses in certain sensitive people.

Although the use of antibiotics to treat mastitis is for an obvious economic benefit, there is a countervailing economic loss to the dairyman from antibiotic residues, since the normal therapies involve infusions over one or two days, followed by milk discard times of two to four days. It is thus desirable to employ an antimicrobial material in the prevention and/or treatment of mastitis which does not leave unwanted residues. In addition, it is important that any broad-spectrum and short-lived antimicrobial does not provoke an inflammatory response in the udder, which would lead to an elevation of somatic cells (macrophage and neutrophilic white cells).

Accordingly, there is a need in the art to resolve the above problems. The present invention accomplishes these objectives, and provides other related advantages.

SUMMARY OF THE INVENTION

Briefly stated, the present invention provides a method for treating or preventing bacterial infections in mammals, including both clinical and subclinical udder infections, in all or in part of a lactating or non-lactating mammal's udder. It also relates to the prophylactic treatment of the mammary gland to aid in suppressing the bacterial growth which leads to such infection. The invention further provides a means of countering the inflammatory process which results from bacterial infection of the udder, and thereby overcoming the reduction of milk production which is associated with inflammation.

The method involves the infusion through a teat and into the mammary gland of an aqueous chlorine dioxide solution comprising from 0.0005% (5 parts per million, ppm) to 0.1000% (1000 ppm), and more preferably from 40 ppm to 400 ppm, of chlorine dioxide in a pharmaceutically acceptable medium or carrier in a volume of from 5 ml to 200 ml. Pharmaceutically acceptable carriers include isotonic saline and other inorganic (e.g., phosphates and sulfates) and organic salts such that the solution is approximately isotonic. The chlorine dioxide solutions of the present invention have a relative molar ratio of chlorine dioxide to residual chlorite of at least 5:1, typically at least 7.5:1, and preferably at least 10:1. Suitable wetting agents (such as nonylphenoxy polyoxyethylene (9)) may also be present.

The chlorine dioxide solution may be provided in a number of ways. For example, it may be formed immediately prior to infusion by combination of a chlorine dioxide liberating compound (such as sodium chlorite) with a suitable aqueous acid, at a pH below 7, in the presence of chloride ion. Carbohydrate triggering substances may be utilized in this formulation. The chlorine dioxide solution can also be provided from an aqueous saline solution in which it has been stored, below a pH of about 5.5. Immediately before infusion, a suitable buffer may optionally be added to the above chlorine dioxide solutions.

DETAILED DESCRIPTION OF THE INVENTION

In one embodiment, the present invention is directed to the use of chlorine dioxide for the prevention, mitigation or cure of bovine mastitis, and/or the alleviation of the associated inflammation, in such a manner as to overcome the rapid loss of antimicrobial activity of the agent which occurs in the presence of significant quantities of organic matter present in the udder. The invention allows for such treatment without the disadvantage associated with every known antibiotic sold for such treatment; that the milk subsequently produced by the mammary gland be excluded from commerce up through four days post-treatment.

The inorganic nature of chlorine dioxide, and its reductive degradation to chloride as a result of its interaction with organic matter (including bacteria), is the basis for the fact that the milk produced in an udder treated according to the present invention need not be discarded. Synthetic antibiotics, unlike the claimed composition, have a prolonged residence in the mammary gland, and milk so contaminated has limitations on its use, as previously explained.

It is important to note that materials may be non-inflammatory (i.e., not provoke inflammation) but not anti-inflammatory (i.e., counter the effects of inflammation). Chlorine dioxide has been found to be non-inflammatory, by virtue of being infusible into the udder without evoking the inflammatory response, as well as being anti-inflammatory. In order to utilize the germ-killing and non-inflammatory qualities of chlorine dioxide, it is preferable to isolate it from chlorous acid and chlorite (which have detrimental effects).

To minimize the negative effects caused by chlorite (and chlorous acid in lower pH solutions), techniques are employed which preferably either a) deliver the soluble chlorine dioxide gas in a solution relatively free of harmful chlorite, or b) employ a pre-infusion chemical reaction whereby the chlorite species has substantially converted to chlorine dioxide leaving relatively little chlorite remaining. In both cases, the relative molar ratio of chlorine dioxide to residual chlorite is at least 5:1, typically at least 7.5:1, and preferably at least 10:1. The concentration of chlorine dioxide in the infusate may be at least 10 mg/liter (ppm), preferably above 20 ppm, and optimally in excess of 40 ppm. As addressed below, the concentration requirement depends, to a significant degree, on the volume of infusate that is to be employed, since it is the total quantity of chlorine dioxide (i.e., concentration times volume) that is critical to the goal of overcoming the neutralizing effects of organic matter in the udder in order to achieve the antimicrobial effects of the chlorine dioxide.

For the delivery of preformed aqueous chlorine dioxide, the following criteria should be met: 1) a pH below about 5.5 to minimize the degradation of chlorine dioxide to chlorite and other species; 2) a concentration of sodium chloride (or equivalent material) sufficient to render the solution approximately isotonic (i.e., about 0.80-about 1.0% NaCl); 3) a package container that is virtually impermeable to, and non-reactive with chlorine dioxide, such as glass and certain grades of polyvinyl chloride ("Barex") and polyvinylidene chloride.

For the preparation of a chlorine dioxide solution immediately before infusion, one cannot use the conventional means of such production, which involves the admixture of a mineral acid with sodium chlorite at such concentrations as to provide rapid evolution of chlorine dioxide, since this results in a very acidic solution with excess residual chlorite. Rather the technique taught by U.S. Pat. No. 4,986,990 (the disclosure of which is hereby incorporated herein by reference) for chlorine dioxide production may be employed. In that patent, concentrations of sodium chlorite and activating acid are both below about 0.01-0.02%, in isotonic saline. Such solutions have been found to be appropriate for use in the mastitis infusion treatment of the present invention. The reactions, upon admixture, are virtually complete within several minutes, and can generate chlorine dioxide solutions in excess of 40 ppm with pH's compatible with the inner udder compartment. The inclusion of small amounts of certain activating sugars (e.g., ribose, galactose, mannose) in the formulation, at levels at or below about 1%, can further increase the speed and efficiency of the reaction. It has been found that this reaction, with or without the addition of sugar triggers, can provide the requisite chlorine dioxide-to-chlorite molar ratios of at least 5:1, necessary to limit tissue irritation.

When 20 ml solutions prepared by such admixture (producing ca. 50 ppm of chlorine dioxide at pH 5.1), are infused into the left side quarters of four cows for seven consecutive times after milking, the somatic cell counts of the subsequent milks demonstrate a minimal inflammatory response, except for a few quarters which had initial high counts. Since seven successive infusions are made, where a mastitis treatment may require only one or two infusions, and since the counts subsequent to the first infusion show no further increase, the chlorine dioxide infusion technique may be properly considered as minimally inflammatory. These data are presented below in Table I. In this study, there are no noticeable irritation effects in the animals, and no abnormalities in the milk.

Another important feature associated with the use of chlorine dioxide infusions for the control of mastitis is its fairly rapid reduction to chloride ion, which is a common component of milk and tissues in general. This reduction occurs by interaction with organic matter, including bacteria. When 1 part of a solution containing 250 ppm of combined chlorine dioxide/chlorite ion is added to 9 parts of milk that is maintained at 37° C. for two hours of incubation, neither of these species can be detected at the 5 ppm sensitivity limit of the procedure. Since chlorite is the first reduction stage of chlorine dioxide, chlorine dioxide infusion into a cow's udder would similarly be reduced to non-detectability by the time the first milk is drawn from the animal (several gallons minimally) at least 6-8 hours after infusion. At any rate, pasteurization of the milk would guarantee the full destruction of the chlorine dioxide to safe chloride ion. When antibiotics are used as traditional mastitis treatments, they are not destroyed in this manner.

TABLE I

SOMATIC CELL COUNTS* BEFORE AND AFTER
7 POST-MILKING INFUSIONS OF 20 ML OF 50 PPM ClO$_2$ SOLUTIONS

| Cow No. | QTR.** | PRE-TREAT. DAY 0 PM | POST-TREATMENT | | | | | | | |
|---|---|---|---|---|---|---|---|---|---|---|
| | | | DAY 1 | | DAY 2 | | DAY 3 | | DAY 4 | |
| | | | AM | PM | AM | PM | AM | PM | AM | PM |
| 405 | LR | 4.22 | 4.23 | 4.16 | 4.45 | 5.95 | 5.79 | 5.13 | 4.51 | — |
| | LF | 2.52 | 3.26 | 7.60 | 4.50 | 6.51 | 5.79 | 5.83 | 5.23 | — |
| 566 | LR | 0.42 | 2.54 | 1.34 | 1.87 | 2.22 | 4.42 | 3.27 | 2.87 | — |
| | LF | 6.28 | 34.7 | 40.9 | 47.4 | 38.4 | 39.2 | 39.2 | 34.3 | — |
| 620 | LR | 5.95 | 13.7 | 12.3 | 10.3 | 4.88 | 8.99 | 6.66 | 6.13 | — |
| | LF | 0.63 | 1.75 | 3.26 | 2.33 | 3.62 | 2.78 | 1.90 | 2.26 | — |
| 624 | LR | 1.35 | 1.33 | 2.04 | 2.61 | 11.06 | 4.15 | 3.80 | 2.27 | — |
| | LF | 0.75 | 0.83 | 1.63 | 3.06 | 4.07 | 3.02 | 1.83 | 2.06 | — |

*Counts are expressed as $10^{-5}$ (i.e., 4.22 in the table = 422,000)
**LR and LF are, respectively, left rear and left front teats Since a sufficient excess of the chlorine dioxide provides microbiocidal activity at a more rapid rate than the rate of depletion of the molecule's oxidizing power by the organic environment, some antimicrobial efficacy may be achieved from the chlorine dioxide despite its rapid reduction by organic matter. This is shown in a pair of studies, one in vitro and one in vivo. In the former, samples of milk are experimentally contaminated with known titers of the *Escherichia coli*. A constant volume of the infected milk is combined with increasing volumes of 46 ppm chlorine dioxide solution, where the ratio of solution to contaminated milk is varied from 1:1 to 10:1. The effect here is to decrease the relative organic milk load in contact with the disinfecting solution. After two contact time periods, 10 minutes and 60 minutes, the milk is assayed for the number of logarithms of organism destroyed. The results of this experiment are presented in Table II.

TABLE II

| TEST SYSTEM* | CONTACT TIME (MIN.) | LOG REDUCTION | (E. COLI) |
|---|---|---|---|
| 1:1 | 10 | 1.04 | |
| | 60 | | 1.85 |
| 1:2 | 10 | 1.36 | |
| | 60 | | 2.46 |
| 1:4 | 10 | 1.57 | |
| | 60 | | 2.78 |
| 1:8 | 10 | 2.90 | |
| | 60 | | 3.74 |
| 1:10 | 10 | 3.11 | |
| | 60 | | 3.66 |

*Dilution ratio of milk:chlorine dioxide solution

Both reduction of relative organic matter in contact with the chlorine dioxide, and increase of contact time, are capable of increasing the antimicrobial effectiveness of the chlorine dioxide solution. These data suggest that the infusion of a sufficient volume of a chlorine dioxide solution into a cow's udder, to overcome the small residual quantity of milk solids remaining in the lower gland (teat canal, cistern and collecting ducts) immediately after milking, could destroy microorganisms present in the environment. Higher chlorine dioxide concentrations in these volumes would similarly enhance the cidal activity. Since residence times of such infusions in the udder are usually greater than the 60-minute contact period studies (i.e., intermilking periods), there would be ample time for the antimicrobial to operate before being chemically neutralized.

For the in vivo evaluation of a chlorine dioxide solution in a cow's udder, to determine whether an infusion volume greater than the normal 10 ml antibiotic infusion would be well tolerated, as well as determine whether any antimicrobial activity could be evident, an experiment is run with subclinically-mastitic cows using 50 ml infusions of a 50 ppm chlorine dioxide solution. Animals are selected on the basis of having chronic subclinical infections which had not responded to therapy with currently available antibiotics. The treatment with a citric-acid activated chlorite solution, in pyrogen-free isotonic saline, involves infusion within approximately one-half hour after milking, once daily, for two days. Two cultures are taken from each quarter treated prior to the initiation of therapy. Post-treatment cultures are taken at 2, 10, and 21 days after the first infusion.

Eight (8) animals are used, having a total of 14 infected quarters. One quarter cultured positive for two pathogens. At 21 days post-infusion 3 of 14 quarters are completely culture-negative. Of these, 2 are positive for *Streptococcus uberis*, and 1 is positive for *Streptococcus bovis*. Of 3 glands positive for *Streptococcus dysgalactiae*, 1 gland shows two negative cultures at 2 and 10 days as a result of treatment. Two of the 7 glands with *Staphylococcus aureus* infections experienced at least one-log reduction in colony forming units by 21 days post-infusion. Considering the fact that two 50 ml infusion volumes are used in this study, the tolerance of this treatment by the animals is noteworthy.

The animals evaluated in this study are *chronically* infected, where irreversible glandular changes often occur, so that the ability of this chlorine dioxide infusion treatment to cure 3 quarters and mitigate the condition in others is considered significant. Infusion of volumes as high as 200 ml of isotonic saline solutions, with chlorine dioxide concentrations higher than the 50 ppm infused in this study, are expected to show increased capacity to effect mastitis cures. Concentrations of chlorine dioxide as high as 1000 ppm have been found effective in laboratory studies where very high levels of organic matter are present. In the absence of chronic mastitic infections, such as newly acquired subclinical mastitis, the ability of the chlorine dioxide solutions to bring about a marked reduction in bacterial counts as well as to effect complete cures is significantly enhanced.

Use of the chlorine dioxide solutions of this invention, with their rapid degradation to chloride salts, further allows for their application as a prophylactic treatment for cows during time and weather periods which predispose to the development of mastitis by the animals. The milk that forms in the gland subsequent to these infusions should not have to be rejected from commercial distribution, or from use in the manufacture of cheese or yogurt, since no antimicrobial residues would remain. There is the further use for these solutions for the prevention of mastitis formation at calving, when a cow is particularly susceptible to the development of infections. A further application for these solutions is during the animal's "dry" period. During this time, there are two periods during which most cows are particularly susceptible to new infections. The first period occurs immediately after the cessation of milking, during which the gland continues to secrete milk, thereby causing leakage of milk and a resulting partially open teat canal. Bacteria can invade the udder through this opening. The second period of increased susceptibility is the periparturient period, which encompasses the week prior to, and the week subsequent to, calving. The infusion of chlorine dioxide solutions could significantly reduce the impact of microbial invasion of the gland, when used prophylactically. There would be no concern that new-born calves would show adverse effects from the milk formed in the treated gland, because of the rapid degradation of the antimicrobial material.

From the foregoing description, one skilled in the art can ascertain the essential characteristics of this invention, and without departing from the spirit and scope thereof, can make various changes and modifications of the invention to adapt it to various usages and conditions. Such modifications and variations are intended to come within the scope of the appended claims.

I claim:

1. A method for treating or preventing a bacterial infection in at least a portion of a mammary gland of a non-human female mammal, comprising infusing into said mammary gland an effective amount of an isotonic composition comprising chlorine dioxide and a pharmaceutically acceptable carrier, wherein (1) the chlorine dioxide is present in the composition in an amount ranging from 5 ppm to 1000 ppm, (2) the molar ratio of chlorine dioxide to any residual chlorite in the composition is at least 5:1, and (3) the pH of the composition is compatible with said mammary gland.

2. The method of claim 1 wherein the female mammal is a cow, a goat or a sheep.

3. The method of claim 1 wherein the female mammal is a cow.

4. The method of claim 1 where the bacterial infection is mastitis.

5. The method of claim 4 wherein the mastitis is subclinical mastitis.

6. The method of claim 4 wherein the mastitis is clinical mastitis.

7. The method of claim 1, wherein the composition is infused through a teat of the mammary gland.

8. The method of claim 7 wherein the composition is infused through the teat in an amount ranging from 5 ml to 200 ml.

9. The method of claim 1 wherein the chlorine dioxide is present in the composition in an amount ranging from 40 ppm to 400 ppm.

10. The method of claim 1 wherein the pharmaceutically acceptable carrier is isotonic saline.

11. The method of claim 1 wherein the composition further includes a wetting agent.

12. The method of claim 1 wherein the molar ratio of chlorine dioxide to any residual chlorite in the composition is at least 7.5:1.

13. The method of claim 1 wherein the molar ratio of chlorine dioxide to any residual chlorite in the composition is at least 10:1.

14. The method of claim 1 wherein the composition is formed immediately prior to infusion by reacting a chlorine dioxide liberating compound with an aqueous acid at a pH below 7 in the presence of chloride ion.

15. The method of claim 1 wherein the composition is prepared immediately prior to infusion by combining a chlorine dioxide solution which has been stored at a pH below 5.5 with the pharmaceutically acceptable carrier.

16. A method for treating or preventing mastitis in at least a portion of a non-human female mammal's udder, comprising infusing into said udder an effective amount of an isotonic composition comprising chlorine dioxide and a pharmaceutically acceptable carrier, wherein (1) the chlorine dioxide is present in the composition in an amount ranging from 5 ppm to 1000 ppm, (2) the molar ratio of chlorine dioxide to any residual chlorite in the composition is at least 5:1, and (3) the pH of the composition is compatible with the inner compartment of said udder.

17. The method of claim 16 wherein the composition is infused into the udder in an amount ranging from 5 ml to 200 ml.

* * * * *